United States Patent
Wu et al.

(10) Patent No.: US 10,045,977 B2
(45) Date of Patent: Aug. 14, 2018

(54) USE OF NALMEFENE IN NON-ALCOHOLIC STEATOHEPATITIS

(71) Applicant: TAIWANJ PHARMACEUTICALS CO., LTD., Zhubei, Hsinchu County (TW)

(72) Inventors: Edwin S C Wu, Research Triangle Park, NC (US); Peter J. S. Chiu, Mill Creek, WA (US); May Mei-chi Hsu, Zhubei (TW)

(73) Assignee: TAIWANJ PHARMACEUTICALS CO., LTD., Zhubei (TW)

( * ) Notice: Subject to any disclaimer, the term of this patent is extended or adjusted under 35 U.S.C. 154(b) by 0 days.

(21) Appl. No.: 15/492,198

(22) Filed: Apr. 20, 2017

(65) Prior Publication Data

US 2017/0304294 A1    Oct. 26, 2017

Related U.S. Application Data

(60) Provisional application No. 62/326,435, filed on Apr. 22, 2016, provisional application No. 62/395,436, filed on Sep. 16, 2016.

(51) Int. Cl.
*A61K 31/485* (2006.01)
*A61K 9/00* (2006.01)

(52) U.S. Cl.
CPC .......... *A61K 31/485* (2013.01); *A61K 9/0053* (2013.01)

(58) Field of Classification Search
CPC ........................... A61K 31/485; A61K 9/0053
USPC ....................................................... 514/282
See application file for complete search history.

(56) References Cited

PUBLICATIONS

Moslehi et al. Acta Physiologica Hungarica 2014, 101(3), 341-352.*
Kawano et al. J. Gastroenterol, 2013, 48, 434-441.*
Vuittonet et al. Am. J. Health. Syst. Pharm., 2014, 71(15), 1265-1276.*

* cited by examiner

*Primary Examiner* — Yevgeny Valenrod
(74) *Attorney, Agent, or Firm* — Ladas & Parry LLP

(57) ABSTRACT

The present invention relates to new medical uses of morphinans such as nalmefene and naltrexone and their related derivatives, pharmaceutical formulations thereof, and use thereof for prevention and treatment of NASH, NAFLD, and/or ASH.

24 Claims, 7 Drawing Sheets

USE OF NALMEFENE IN NON-ALCOHOLIC STEATOHEPATITIS

CROSS REFERENCES APPLICATIONS

This application claims the benefit of U.S. Provisional Patent Applications No. 62/326,435 filed Apr. 22, 2016 and 62/395,436 filed Sep. 16, 2016, the contents of which are incorporated herein by reference.

BACKGROUND OF THE INVENTION

The present invention relates to a new method of use of morphinans. The present invention relates to naltrexone or 17-cyclopropylmethyl-4,5α-epoxy-6-oxomorphinan-3,14-diol and nalmenfene or 17-cyclopropylmethyl-4,5α-epoxy-6-methylenemorphinan-3,14-diol or nalmefene, and their analogs, and pharmaceutical formulations thereof, and use thereof for prevention and treatment of NASH (non-alcoholic steatohepatitis), NAFLD (non-alcoholic fatty liver disease) and ASH (alcoholic steatohepatitis).

In PCT publication WO 03/097608, we have described a number of new medical uses of opioid and opioid-like compounds, including naltrexone and nalmefene. In PCT publication WO WO2006029167, we have described a number of new medical uses of 17-cyclopropylmethyl-4,5α-epoxy-6-methylenemorphinan-3,14-diol.

Recent advances in the research of neurodegenerative diseases of the central nervous system have revealed that the opioids may play a role in modulating the expression of inflammatory factors such as proinflammatory cytokines, free radicals and metabolites of arachidonic acid in microglia and in the mediation of immune-related neurodegeneration [*Adv. Exp. Med. Biol.* 1996, 402: 29-33; *Mov. Disord.* 1997; 12: 855-858] and neuropathic pain [Hutchinson M R, et al. *Eur J Neurosci.* 2008; 28:20-299]. A Chinese Patent application (CN102048733) claims the use of nalmefene for treatment of fatty liver due to the high fat diet via injection.

In this application, we disclose that nalmefene and naltrexone have demonstrated its efficacy in preventing and treating NAFLD, NASH, and ASH.

The present invention provides a method of the prevention of inflammatory hepatic injury in NAFLD and its progression to NASH.

The emerging epidemic of obesity and metabolic syndrome has contributed to the increased prevalence of NASH as what is now considered to be the leading cause of chronic liver disease in the Western world (Clark, J. M., et al., *Nonalcoholic fatty liver disease. Gastroenterology*, 2002; 122: 1649-1657). NASH affects 2 to 5 percent of Americans. An additional 10 to 20 percent of Americans have fat in their liver, but no inflammation or liver damage, a condition called "fatty liver." Although having fat in the liver is not normal, by itself it probably causes little harm or permanent damage. If fat is suspected based on blood test results or scans of the liver, this condition is called nonalcoholic fatty liver disease (NAFLD). If a liver biopsy is performed in this case, it will show that some people have NASH while others have simple fatty liver. NASH or NAFLD resembles ASH (Alcoholic Steatohepatitis) or ALD (alcoholic liver disease) respectively but occurs in people who drink little or no alcohol [Ludwig, J., et al., *Nonalcoholic steatohepatitis: Mayo Clinic experiences with a hitherto unnamed disease. Mayo Clin Proc,* 1980; 55: p. 434-438].

While the underlying causes of NASH remain unclear, several factors such as insulin resistance, release of toxic inflammatory proteins by fat cells (cytokines), and oxidative stress (deterioration of cells) inside liver cells may contribute to the morbidity of NASH (http://digestive.niddk.nih.gov/ddiseases/pubs/nash).

The exact mechanisms responsible for pathogenesis and progression of fatty liver disease are not entirely clear. Several studies have demonstrated that hepatic steatosis predisposes animals to greater injury in the presence of a subsequent stress such as endotoxemia. Since it is widely accepted that the transition from steatosis to steatohepatitis (NAFLD to NASH) is dependent upon a "second hit" such as oxidative stress or endotoxemia (Wanless I R, Shiota K. The pathogenesis of nonalcoholic steatohepatitis and other fatty liver diseases: a four-step model including the role of lipid release and hepatic venular obstruction in the progression to cirrhosis. *Semin Liver Dis.* 2004; 24:99-106; Duvnjak M, et al. *Pathogenesis and management issues for non-alcoholic fatty liver disease. World J Gastroenterol.* 2007; 14; 13:4539-4550). It is now commonly accepted that the progression occurs as part of a "two hit" mechanism in which the first hit is lipid accumulation in the hepatocytes (steatosis) (Day C P, James O F. *Steatohepatitis: a tale of two "hits"? Gastroenterology* 1998; 114: 842-845; Sanches SC et al. *Nonalcoholic Steatohepatitis: A Search for Factual Animal Models. Biomed Res Int.* 2015; 2015:574832). The second hit is presumed to be oxidative, endotoxemia or inflammatory stress. With repeated stresses the enhanced inflammatory response leads to hepatic injury and the onset of fibrosis. While the definitive treatment for fatty liver disease is the reversal of the steatosis through weight reduction and restoration of insulin sensitivity, this is not generally complete nor even practical in many cases.

Currently, there are no FDA-approved treatments for fatty liver disease and NASH or ASH. Experimental approaches under clinical evaluation in patients with NASH include antioxidants (for example, vitamin E), selenium, and betaine, as well as newer antidiabetic medications. The need for specific pharmacotherapy is now acknowledged by practitioners, the pharmaceutical industry, and regulators, and is greatly anticipated by patients. The result is a clear move away from products developed second hand for NASH (such as pioglitazone or metformin) or from generic, non-specific hepatoprotectants (such as pentoxifylline, ursodeoxycholic acid, or antioxidants) toward molecules developed and tested specifically for NASH that aim to correct one or several of the pathways of liver injury in this disease. The two most advanced molecules, obeticholic acid and elafibranor, have shown encouraging results on improving hepatic histology. Both compounds appear to clear NASH, with obeticholic acid improving liver fibrosis and elafibranor improving the glycemic and lipid profile [Ratziu V., *Novel Pharmacotherapy Options for NASH. Dig Dis Sci.* 2016 Mar. 22. (Epub ahead of print)].

Methionine-Choline-Deficient (MCD) diet mouse model is a well accepted model of NASH, as described above (cf. Rivera C A, et al. 2007; Sanches S C et al. *Nonalcoholic Steatohepatitis: A Search for Factual Animal Models. Biomed Res Int.* 2015; 2015:574832). Consequently the MCD diet mice have been widely used to test hepatoprotectant effects of compounds against NAFLD/NASH.

Nalmefene demonstrated efficacy in preventing inflammatory liver damage in the MCD rat model, followed by a second hit with LPS.

Alcoholic liver disease (ALD) Alcoholic liver disease (ALD) is a leading cause of liver-related morbidity and mortality worldwide (Arsene et al. *Hepatol Int.* 2016; 10:538-552). The clinical and pathologic spectrum of ALD ranges from alcoholic fatty liver disease (alcoholic steatosis) to cirrhosis (Saberi et al. *J Clin Transloat Hepotol.* 2016; 4:113-122). ALD can be divided into alcohol-induced steatosis (microvesicular, macrovesicular), alcoholic steatohepatitis (ASH) and alcoholic cirrhosis. The pathology of ALD resembles that of NAFLD/NASH. ALD and NAFLD have a similar pathologic spectrum, and they have been described to coexist in the clinical setting (Toshikuni et al World J Gastroenterol 2014; 20:8393-8406; Brunt and Tiniakos. World J Gastroenterol 2010; 16:5286-5296). Acute and chronic ingestion of alcohol lead to a strong elevation of portal and systemic levels of endotoxin in animal models and humans (Porlesok et al. *J Hepotol* 2000; 32:742-747). Endotoxin is a crucial mediator of liver injury in alcoholic liver disease as demonstrated by the significant reduction of alcoholic liver injury following elimination of the Gram-negative microbiota by antibiotics, and the sensitization to LPS-induced liver injury following long-term ethanol exposure. The elevation of endotoxin appears to be predominantly caused by two mechanisms. First, alcohol consumption leads to changes in the intestinal microbiota with bacterial overgrowth in the upper gastrointestinal tract (Hauge et al. *Digestion* 1997; 58:591-595). Second, alcohol ingestion is known to disrupt the intestinal epithelial barrier causing enhanced permeability thus allowing increased levels of LPS to enter the portal circulation (Bjornason et al. *Lancet* 1984; 1:179-182). Kupffer cells have been established as a crucial cellular target of LPS in ethanol-induced liver injury (Adachi et al. *Hepatology* 1994; 20:453-460). Experimental models of ALD have revealed that translocation of bacterial products across the intestinal barrier to the portal circulation triggers inflammatory responses in the liver and contributes to steatohepatitis. The most effective measure to manage ASH is alcohol abstinence by alcoholic patients. Steroids have some short term benefit in treatment of severe ASH, but long term effect is unclear due to numerous side effects. Consequently, there is an urgent need to focus discovery efforts on effective therapeutic interventions for ASH.

SUMMARY OF INVENTION

The present invention relates to morphinan compounds, and pharmaceutical formulations thereof, and use thereof for prevention and treatment of NASH (non-alcoholic steatohepatitis), NAFLD (non-alcoholic fatty liver disease), and ASH (alcoholic steatohepatitis).

The present invention relates to use of a morphinan compound according to the formula (I) in treatment of NALFD, NASH and ASH or conditions or for the production of medicaments, for treatment of such conditions wherein:

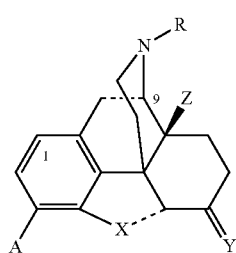

(I)

A can be OH or OCH3; R can be H, CH3, or cyclopropylmethyl; X is the oxygen atom, Y is O or CH2, Z can be H or OH. The compounds according to the formula (I) can be enantiomers, diastereoisomers, and pharmaceutically acceptable salts thereof.

Formula (I) can be a structure such as one of the following structures:

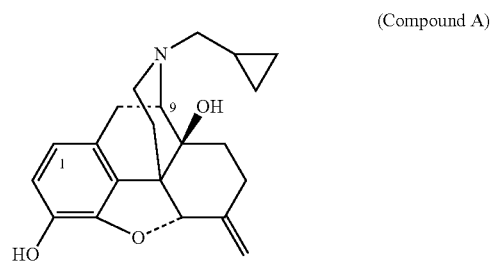

(Compound A)

Particularly preferred is Compound A (nalmefene), the compound (I) wherein A is OH, R is cyclopropyl, methyl, X is O, Y is CH2, and Z is OH.

Formula (I) can be a structure such as one of the following structures:

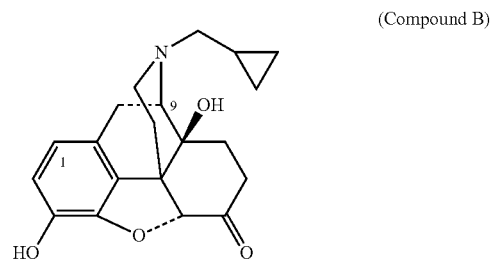

(Compound B)

Particularly preferred is Compound B (naltrexone), the compound (I) wherein A is OH, R is cyclopropylmethyl, X is O, Y is O, and Z is OH.

Figure 5:
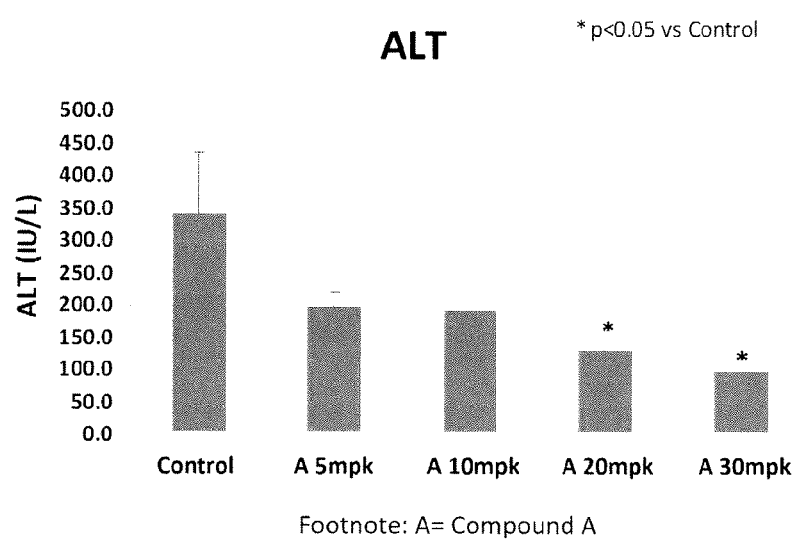
FIG. 5 shows dose-dependent Prevention of liver damage in rats with steatotic livers.
Figure 6:
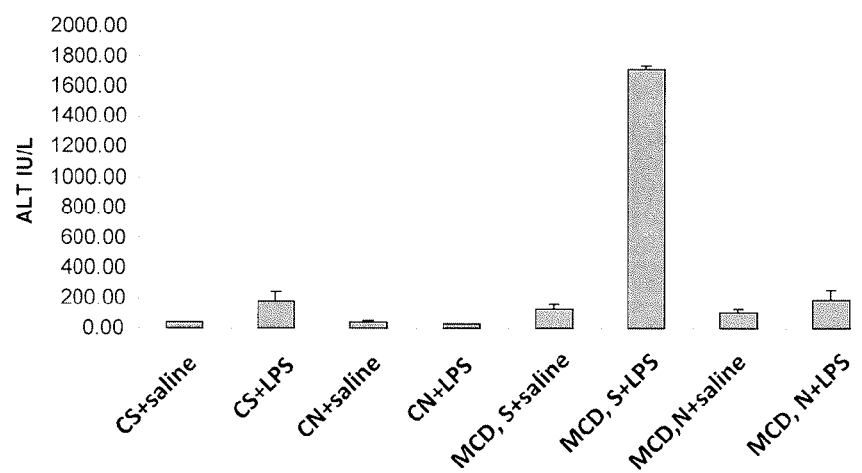

The experiment at 20 mg was repeated with n=5/group as shown in FIG. 6 and produced the same results to that in FIG. 5.

FIG. 6 shows dose-dependent Prevention of liver damage in rats with steatotic livers at 20 mg/Kg (N=Compound A).

Figure 7:
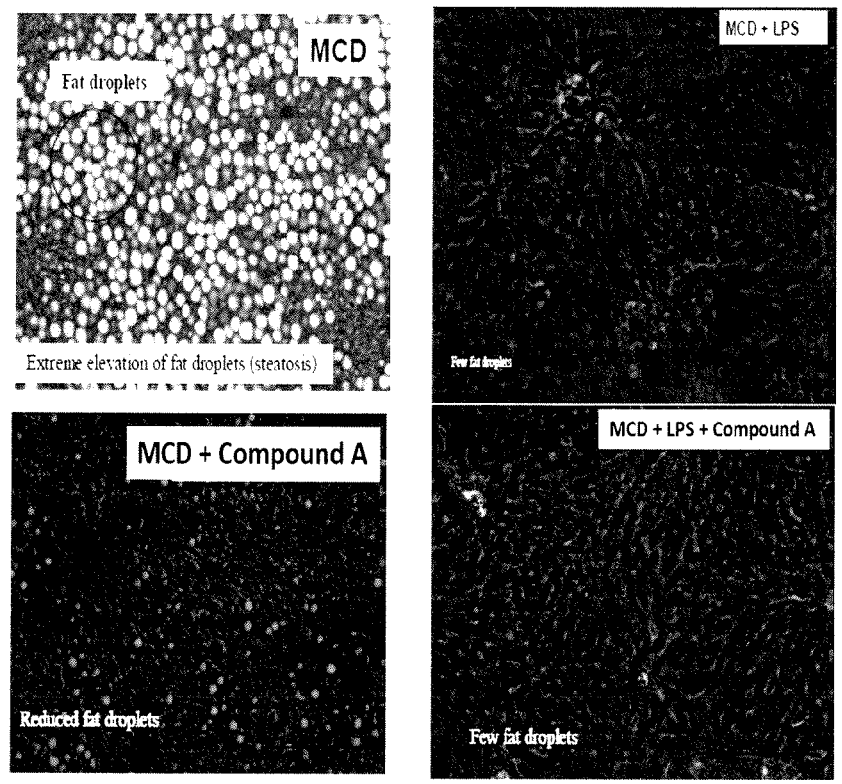

FIG. 7 shows liver injury assessed by histopathological examination of Compound A/LPS treated rats from this experiment. Histopathology indicates that Compound A prevents hepatic fat accumulation in treated rats as compared to the control. FIG. 7 indicates that there are improvement of steatosis by Compound A and improvement of liver injury from LPS-treated fatty liver injury. In FIG. 7: a) Left top [control (MCD treated rats)]: indicated there is macrovesicular steatosis with a bit of microvesicular steatosis; b) Left bottom [MCD and Compound A treated rats]: slight periportal chronic inflammation (mild nonspecific chronic hepatitis); c) Right Top: MCD+LPS treated rats: black dots (arrow) are dying hepatocytes; the light shade area (rectangle) indicates necrosis. There is hemorrhage and periportal (zone 1) necrosis. No significant congestion or loss of architecture; and d) Right bottom [MCD+LPS+Compound A treated rats]: slight periportal chronic inflammation.

DETAILED DESCRIPTION OF THE INVENTION

Treatments or medicaments produced according to the invention include those for preventing or treating NASH (non-alcoholic steatohepatitis), NAFLD (non-alcoholic fatty liver disease), and/or (ASH) alcoholic steatohepatitis.

According to other embodiments of the present invention, the present invention relates to methods of preventing or treating NASH, NAFLD, and/or ASH, comprising administering to a subject in need thereof, a pharmaceutical composition comprising a therapeutically effective amount of one or more of the specified compounds. The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, patent applications, patents and other references cited herein are incorporated by reference in their entirety for the teachings relevant to the sentence and/or paragraph in which the reference is presented.

The term "opioid" as used herein refers to compounds that exhibit opium or morphine-like properties, including agonist and antagonist activity wherein such compounds can interact with stereospecific and saturable binding sites in the brain and other tissues. Pharmacological properties have previously included drowsiness, respiratory depression, changes in mood and mental clouding without a resulting loss of consciousness. The term "opioid-like" as used herein refers to compounds that are similar in structure and/or pharmacological profile to known opioid compounds.

"Treat" or "treating" as used herein refers to any type of treatment that imparts a benefit to a patient afflicted with a disease, including improvement in the condition of the patient (e.g., in one or more symptoms), delay in the progression of the condition, prevention or delay of the onset of the disease, etc.

As used herein, a "pharmaceutically acceptable" component (such as a salt, carrier, excipient or diluent) means that the compound or composition is suitable for administration to a subject to achieve the treatments described herein, without unduly deleterious side effects in light of the severity of the disease and necessity of the treatment.

As used herein the term "prophylaxis", "prevention" or "preventing" means administering a pharmaceutical to a subject prior to the exhibition of relevant symptoms to reduce the risk of a disease manifesting itself or to reduce its severity if it does manifest itself.

"Therapeutically effective amount" as used herein refers to an amount necessary to prevent, delay or reduce the severity of the condition of interest and also includes an amount necessary to enhance normal physiological functioning.

Active compounds of the present invention can be water soluble and can also comprise known water-soluble opioid and opioid-like derivatives.

Compounds of the present invention can possess an asymmetric carbon atom(s) and therefore are capable of existing as enantiomers or diastereoisomers. Thus, compounds of the present invention include enantiomers and diastereoisomers as well as pharmaceutically acceptable salts of the compounds of the present invention.

Active compounds of the present invention can be administered. For example, active compounds of the present invention can be coadministered with compounds now known, or later identified, to be useful for the prevention and or treatment of NASH, NAFLD, and/or ASH.

As noted above, nalmefene and naltrexone are well documented compounds and commercially available. Other compounds of use in the present invention may be obtained by modification of nalmefene by routine chemical methods or by use of techniques analogous to those described in PCT Publication WO 03/097608.

The term "active agent" as used herein, includes the pharmaceutically acceptable salts of the compound. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. In other particular embodiments, pharmaceutically acceptable salts are formed with malic acid. In particular embodiments, pharmaceutically acceptable salts are formed with hydrochloric acid.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

Pharmaceutical Formulations

The opioid and opioid-like compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

It will be appreciated that certain compounds of the above formulas can possess an asymmetric carbon atom(s) and are thus capable of existing as enantiomers. Unless otherwise specified, this invention includes such enantiomers, including racemates. The separate enantiomers may be synthesized from chiral starting materials, or the racemates can be resolved by procedures that are well known in the art of chemistry such as chiral chromatography, fractional crystallization of diastereomeric salts and the like.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. In one particular embodiment, a pharmaceutical composition comprises less than 80% by weight of active compound. In other particular embodiments, a pharmaceutical composition comprises less than 50% by weight of active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, tablets, dragees, or syrups each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3(6):318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

The present invention may also be formulated into a sustained-release preparation. A sustained-release composition includes, but is not limited to, those in which the active ingredient is bound to an ion exchange resin which is optionally coated with a diffusion barrier to modify the release properties of the resin.

Carriers and/or diluents which may be used include vaseline, lanoline, glycerin, vegetable oils, or fat emulsions, polyethylene glycols, alcohols, transdermal enhancers, natural or hardened oils or waxes, and combinations of two or more thereof.

Methods of Use

In addition to the compounds of the formulas described herein, the present invention also provides useful therapeutic methods. For example, the present invention provides a method of treating NASH, NALFD, and/or ASH.

Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Any mammalian subject in need of being treated according to the present invention is suitable. Human subjects are preferred. Human subjects of both genders and at any stage of development (i.e., neonate, infant, juvenile, adolescent, adult) can be treated according to the present invention.

As noted above, the present invention provides pharmaceutical formulations comprising the compounds of formulae described herein, or pharmaceutically acceptable salts thereof, in pharmaceutically acceptable carriers for any suitable route of administration, including but not limited to, oral, rectal, topical, buccal, parenteral, intramuscular, intradermal, intravenous, and transdermal administration.

According to the present invention, methods of this invention comprise administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the compounds of the present invention can be administered to the subject in an amount ranging from a lower limit from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, or 10% to an upper limit ranging from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% by weight of the composition. In some embodiments, the compounds comprise from about 0.05 to about 95% by weight of the composition. In other embodiments, the compounds comprise from about 0.05 to about 60% by weight of the composition. In still other embodiments, the compounds comprise from about 0.05 to about 10% by weight of the composition.

The therapeutically effective dosage of any specific compound will vary somewhat from compound to compound, patient to patient, and will depend upon the condition of the patient and the route of delivery. As a general proposition, a dosage from about 0.1 to about 50 mg/kg will have therapeutic efficacy, with still higher dosages potentially being employed for oral and/or aerosol administration. Toxicity concerns at the higher level may restrict intravenous dosages to a lower level such as up to about 10 mg/kg, all weights being calculated based upon the weight of the active base, including the cases where a salt is employed. Typically, a dosage from about 0.5 mg/kg to about 5 mg/kg will be employed for intravenous or intramuscular administration. A dosage from about 1 mg/kg to about 50 mg/kg may be employed for oral administration.

In particular embodiments, compounds of the present invention may be administered at a daily dosage of from about 0.1 mg to about 20 mg per kg of animal body weight, which can be given in divided doses q.d. to q.i.d. or in a sustained release form. For humans, the total daily dose may be in the range of from about 1 mg to about 1,400 mg, for example from 1 to 50 mg daily and in other particular embodiments, the total daily dose is in the range of from about 10 mg to about 100 mg. In still other embodiments, the unit dosage forms suitable for oral administration may comprise about 1 mg to about 1,400 mg of the compound optionally admixed with a solid or liquid pharmaceutical carrier or diluent. The compounds of the present invention can be administered in any amount appropriate to administer to the subject for treatment of the condition desired to be treated as determined by one of ordinary skill in the art by reference to the pertinent texts and literature and/or by using routine experimentation. (See, for example, Remington, *The Science And Practice of Pharmacy* (9th Ed. 1995). However, in general, satisfactory results are obtained when the compounds of the invention are administered at a daily dosage of from about 0.1 mg to about 20 mg per kg of animal body weight, preferably given in divided doses 1 to 4 times a day or in sustained release form.

The foregoing is illustrative of the present invention, and is not to be construed as limiting thereof. The invention is defined by the following claims, with equivalents of the claims to be included therein.

EXAMPLE 1

Synthesis of the Compounds of the Present Invention

Compound A (nalmefene) and Compound B (naltrexone) are commercially available.

EXAMPLE 2

Compound A Reduces Stimulated Release of TNF-α and MAPK Phosphorylation in LPS-Treated Kupffer Cells The primary motors of the inflammatory response in the liver are the Kupffer cells. TNF-α has been known to play an important role in liver damage and its plasma concentration has been correlated with the severity of liver damage. p38 phosphorylation is a key step in one of the main pathways leading to pro-inflammatory mediator production by Kupffer cells.

2.1 Experimental Design

Kupffer cells were isolated by enzymatic digestion and purified by centrifugal elutriation from normal rats and cultured overnight. They were then stimulated with *E. coli* LPS either without or with Compound A added to the medium. TNF-α content in the supernatant was measured at 2, 4, and 6 hours.

2.2 Results

Figure 1:
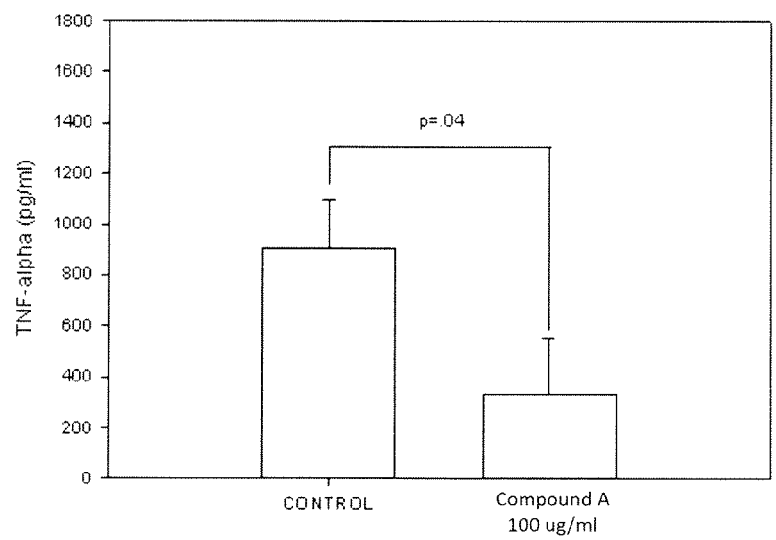
FIG. 1 shows reduction of TNF-α release in Kupffer Cells.
Figure 2:
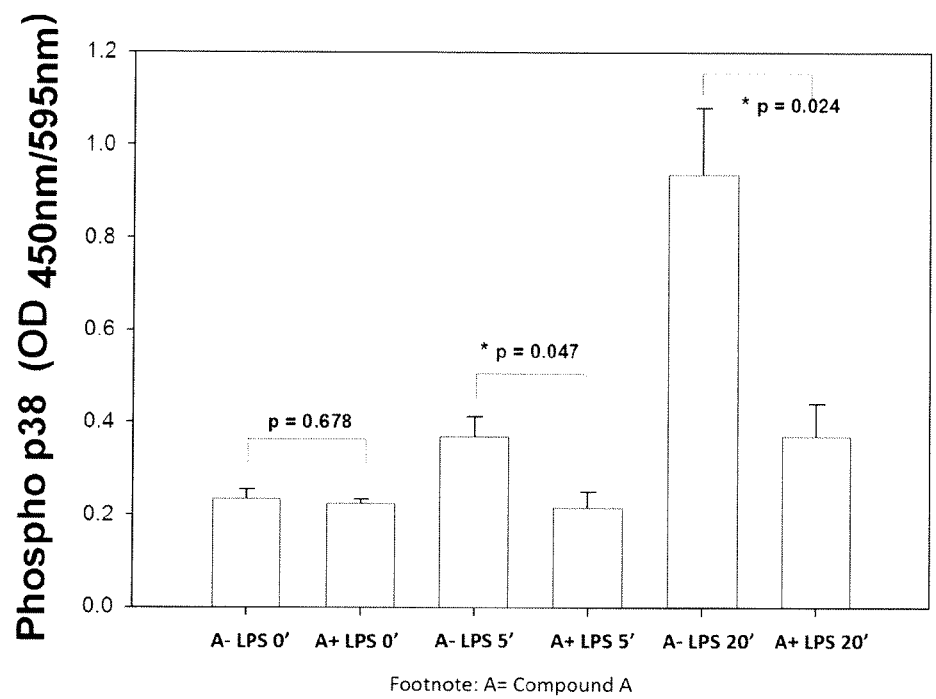
FIG. 2 shows reduction of LPS-induced p38 MAP kinase phosphorylation in Kupffer cells. p38 MAP kinase phosphorylation was monitored at 5 and 20 min; Compound A (A=Compound A) dosed at 100 ng/mL; n=3 replicates.

Compound A inhibited the LPS/time-dependent increase in TNF-α released by Kupffer cells. [After 2 h, excessive accumulation of TNF-α in the cells interfered with the results]. (FIG. 1). Compound A also reduced LPS-induced p38 MAP kinase phosphorylation in Kupffer cells (FIG. 2).

EXAMPLE 3

In Vivo Efficacy Study in STAM Model of Non-Alcoholic Steatohepatitis (NASH)

General Procedure NASH was induced in male C57BL/6 mice by a single subcutaneous injection of 200 μg streptozotocin solution 2 days after birth and feeding with high fat diet (HFD, 57 kcal % fat, Cat# HFD32, CLEA Japan, Japan) after 4 weeks of age. The animals were divided into groups of six each and were orally administered vehicle (1% Tween80) at 10 mL/kg or Telmisartan at 10 mg/kg twice daily from 6 to 9 weeks of age. Similarly, Compound A/Nalmefene (NMN) and Compound B/Naltrexone (NTX) were administered subcutaneously at 5 mg/kg twice daily. The animals were sacrificed at week 9. Mean body weight in the Telmisartan group gradually decreased during the treatment period. During the treatment period, one out of six mice was found dead in the NMN group before reaching week 9. The Telmisartan group tended to show decrease in mean body weight on the day of sacrifice compared with the Vehicle group. There were no significant differences in mean body weight on the day of sacrifice between the Vehicle group and any of the treated groups (data not shown).

Figure 3:
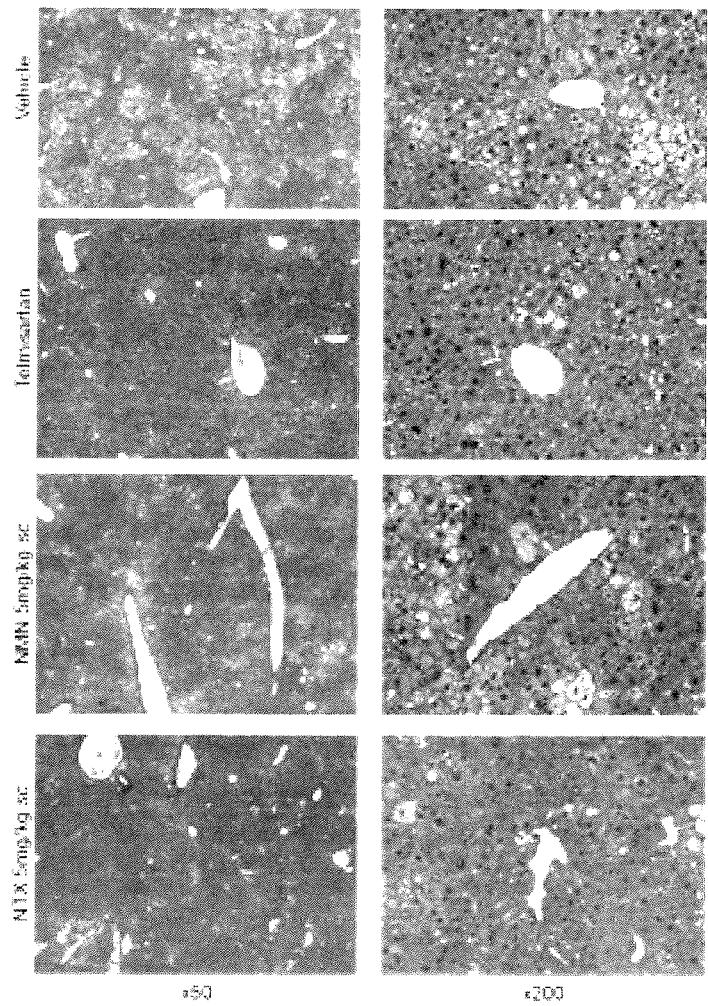
FIG. 3 sets out representative photomicrographs of HE-stained sections of livers from STAM model of NASH. Sections were cut from paraffin blocks of liver tissue pre-fixed in Bouin's solution and stained with Lillie-Mayer's Hematoxylin and eosin solution. NAFLD Activity score (NAS) was calculated according to the criteria of Kleiner (Kleiner et al, 2005).
Figure 4A:
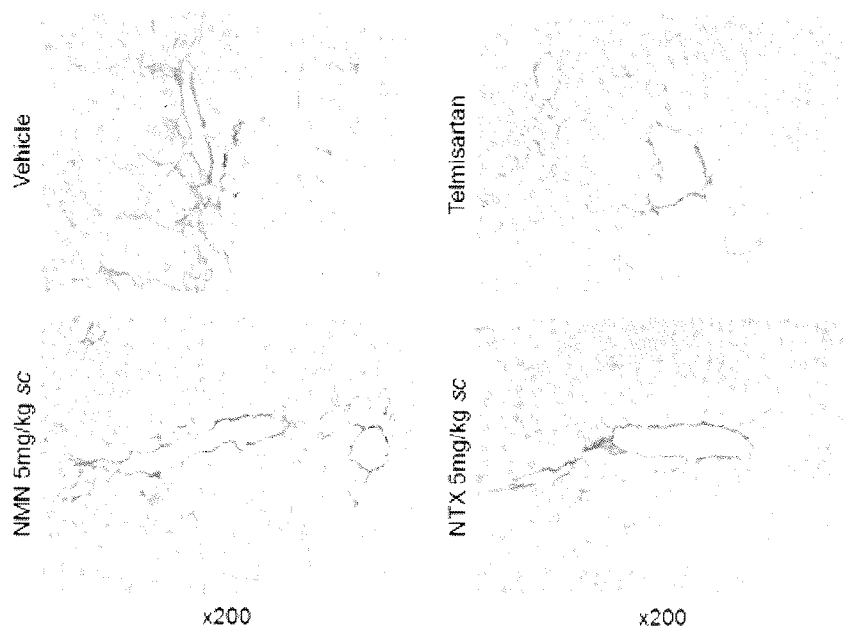
FIGS. 4A-4B shows sirius red-positive area (%) in STAM model of NASH. a) Representative Sirius red micrographs. To visualize collagen deposition, Bouin's-fixed left lateral liver sections were stained using picro-Sirius red solution (Waldeck, Germany). b) For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA). Individual values and mean±SEM for each treatment group are presented.
Figure 4B:
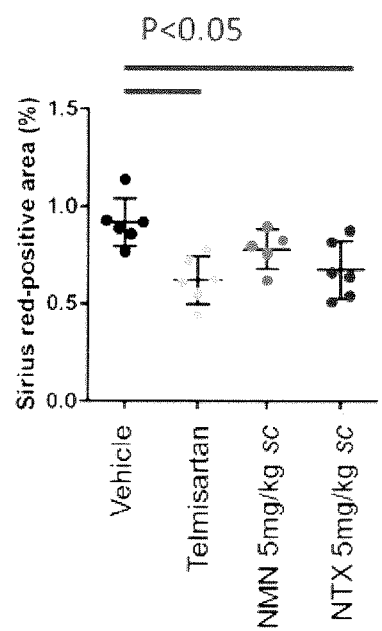

Representative photomicrographs of hematoxylin and eosin (HE)-stained sections of livers from Vehicle, Telmisartan, NTX, and NMN are shown in FIG. 3. Liver sections from the Vehicle group exhibited micro- and macrovesicular fat deposition, hepatocellular ballooning and inflammatory cell infiltration. The Telmisartan and NTX groups showed significant decreases in NAS (NAFLD Activity Score) compared with the Vehicle group. The NMN group tended to show decrease in NAS compared with the Vehicle group.

TABLE 1a

Histopathology and NAFLD Activity score in STAM Model of NASH

| | Vehicle | Telmisartan | Nalmefene | Naltrexone |
|---|---|---|---|---|
| Steatosis | 1.17 ± 0.17 | 0.50 ± 0.22* | 0.80 ± 0.49 | 0.50 ± 0.22* |
| Inflammation | 2.33 ± 0.33 | 1.17 ± 0.48 | 1.80 ± 0.20 | 1.67 ± 0.33 |
| Ballooning | 1.50 ± 0.22 | 1.00 ± 0.26 | 0.40 ± 0.24* | 0.00 ± 0.00* |
| NAS | 5.00 ± 0.37 | 2.67 ± 0.56* | 3.00 ± 0.63* | 2.17 ± 0.40* |

NAS: NAFLD activity score (see Table 1b)
All values represent mean ± SEM for 5 (nalmefene) or 6 animals.
*P < 0.05 vs Vehicle control; two-tailed un-paired t test.

TABLE 1b

NAS score measurement

| Measurements | Score | Extent |
|---|---|---|
| Steatosis | 0 | <5% |
| | 1 | 5-33% |
| | 2 | >33-66% |
| | 3 | >66% |
| Lobular Inflammation | 0 | No foci |
| | 1 | <2 foci/200x |
| | 2 | 2-4 foci/200x |
| | 3 | >4 foci/200x |
| Hepatocyte Ballooning | 0 | None |
| | 1 | Few balloon cells |
| | 2 | Many cells/prominent ballooning |

Liver sections from the Vehicle group showed increased collagen deposition in the pericentral region of liver lobule (Table 1a; FIG. 3). The fibrosis area (Sirius red-positive area) was significantly decreased in the Telmisartan and NTX groups compared with the Vehicle group. NMN-treated group tended to shown decrease in fibrosis area compared with the Vehicle group.

EXAMPLE 4

The Methionine-Choline-Deficient (MCD) Diet Rat Model (Cf. Szabo G. Et al 2005)

4.1 Experimental Design

20 Sprague Dawley rats were administered with Compound A by oral gavage once daily at 0, 5, 10, 20 or 30 mg/kg (4 rats/group) for 4 weeks. All animals were fed a methionine/choline deficient (MCD) diet (from Dyets, Inc) five times per week during the feeding period in order to produce a diet-induced fatty liver. Rats were weighed daily as well as food intake. At the end of four weeks, the rats were administered 2 mg/kg E coli endotoxin (LPS) IP and 6 hours later the rats were euthanized and liver tissue and serum collected. Liver and was harvested at time of death as was blood. Histology samples were also taken.

4.2 Results

As shown in FIG. 5, Compound A demonstrated a dose-dependent prevention of liver injury following dosing of LPS in fatty liver rats (n=3/group; mpk=mg/kg; A=Compound A). In the absence of Compound A treatment, serum ALT levels were 339 U/L. LPS caused a pathological increase in ALT. Treatment of 5 and 10 mg/kg Compound A treatment decreased the elevated ALT levels by nearly 50%, but this was not statistically significant due to the small n (n=3 per group) in this pilot dosing study. However, at 20 and 30 mg/kg there was a further decrease that was significant even with low numbers (p<0.05). With 30 mg/kg ALT was 94.9+/−5.5 U/L. These results demonstrate a dose-dependent prevention of liver injury by COMPOUND A following endotoxemia in rats with non-alcoholic fatty liver disease.

The invention claimed is:

1. A method of treating, NASH, which comprises administering to a human or animal in need thereof a therapeutic amount of a compound of the formula (I), wherein:

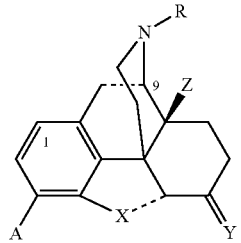
(I)

A is OH or OCH3, R is H, CH3, or cyclopropylmethyl;
X is the oxygen atom, Y is CH2 or oxygen, Z is H or OH, said compounds being administered as a racemic mixture or as enantiomers, diastereoisomers, or pharmaceutically acceptable salts.

2. The method of claim 1, wherein the compound of Formula (I) has one of the following structures:

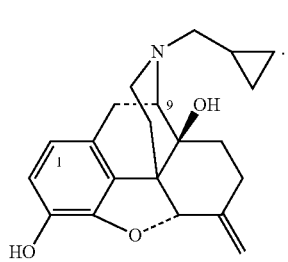
(Compound A)

3. The method of claim 1, wherein the compound of Formula (I) has one of the following structures:

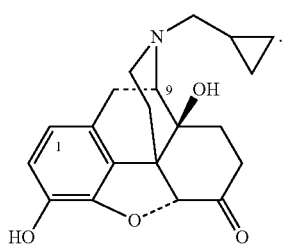

Compound B

4. A method as claimed in claim 1, wherein said compound is Compound A (nalmefene).

5. A method as claimed in claim 1, wherein said compound is Compound B (naltrexone).

6. A method of treating NAFLD, which comprises administering to a human or animal in need thereof a therapeutic amount of a compound of the formula (I), wherein:

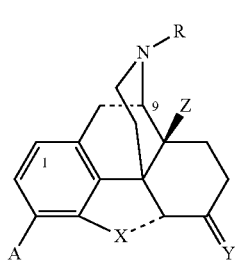

(I)

A is OH or OCH3, R is H, CH3, or cyclopropylmethy;

X is the oxygen atom, Y is CH2 or oxygen, Z is H or OH, said compounds being administered as a racemic mixture or as enantiomers, diastereoisomers, or pharmaceutically acceptable salts.

7. A method of treating-ASH, which comprises administering to a human or animal in need thereof a therapeutic amount of a compound of the formula (I), wherein:

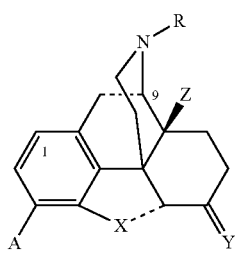

(I)

A is OH or OCH3, R is H, CH3, or cyclopropylmethyl;

X is the oxygen atom, Y is CH2 or oxygen, Z is H or OH, said compounds being administered as a racemic mixture or as enantiomers, diastereoisomers, or pharmaceutically acceptable salts.

8. The method of claim 1, wherein the compound is administered orally.

9. The method of claim 1, wherein the compound is administered parenterally.

10. A method as claimed in claim 1 wherein said compound is administered in a daily dose of from 1 mg to 100 mg.

11. The method of claim 6, wherein the compound of Formula (I) has one of the following structures:

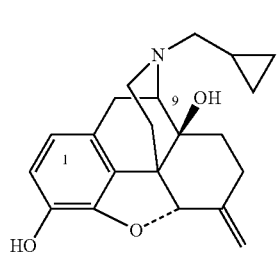

(Compound A)

12. The method of claim 6, wherein the compound of Formula (I) has one of the following structures:

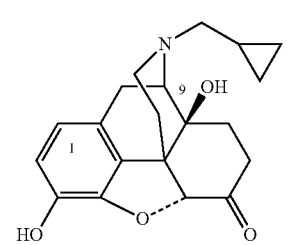

Compound B

13. A method as claimed in claim 6, wherein said compound is Compound A (nalmefene).

14. A method as claimed in claim 6, wherein said compound is Compound B (naltrexone).

15. The method of claim 6, wherein the compound is administered orally.

16. The method of claim 6, wherein the compound is administered parenterally.

17. A method as claimed in claim 6 wherein said compound is administered in a daily dose of from 1 mg to 100 mg.

18. The method of claim 7, wherein the compound of Formula (I) has one of the following structures:

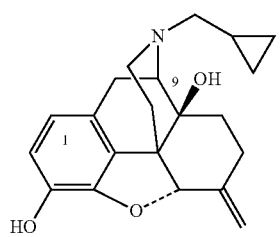

(Compound A)

19. The method of claim 7, wherein the compound of Formula (I) has one of the following structures:

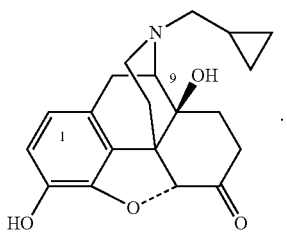

Compound B

20. A method as claimed in claim 7, wherein said compound is Compound A (nalmefene).

21. A method as claimed in claim 7, wherein said compound is Compound B (naltrexone).

22. The method of claim 7, wherein the compound is administered orally.

23. The method of claim 7, wherein the compound is administered parenterally.

24. A method as claimed in claim 7 wherein said compound is administered in a daily dose of from 1 mg to 100 mg.

\* \* \* \* \*